| United States Patent [19] | [11] | 4,438,200 |
|---|---|---|
| Taubman et al. | [45] | Mar. 20, 1984 |

[54] METHOD FOR THE PREPARATION OF GLUCOSYLRANFERASE

[75] Inventors: Martin A. Taubman, Newton; Daniel J. Smith, Natick, both of Mass.

[73] Assignee: Forsyth Dental Infirmary for Children, Boston, Mass.

[21] Appl. No.: 416,869

[22] Filed: Sep. 13, 1982

[51] Int. Cl.³ .............................................. C12N 9/10
[52] U.S. Cl. .................................. 435/193; 435/814; 435/815
[58] Field of Search ........................ 435/193, 101, 815

[56] References Cited

U.S. PATENT DOCUMENTS 4,250,262  2/1981  Taubman et al. .................... 435/193
4,340,673  7/1982  Stoudt et al. .......................... 435/97

Primary Examiner—Lionel M. Shapiro
Attorney, Agent, or Firm—Richard P. Crowley

[57] ABSTRACT

A method of preparing a purified glucosyltransferase (GTF) for use in immunization against dental caries, which method comprises: culturing a Streptococcus mutans in a medium containing glucose and dialyzable nutrients to form a mixture of culture cells and supernatant; recovering the supernatant by the removal of the culture cells; admixing the recovered supernatant with a water-insoluble, polymerized polysaccharide as solid particulate material for a period of time, to provide a GTF, solid particulate complex; recovering the GTF complex in solid particulate form by filtration; washing the solid GTF complex to remove unbound GTF and medium components; removing GTF from the solid particulate material by a denaturing solvent; recovering the water-insoluble particulate material for reuse in the method; and recovering the GTF from the water-insoluble polysaccharide and purifying the recovered GTF.

14 Claims, No Drawings

METHOD FOR THE PREPARATION OF GLUCOSYLRANFERASE

BACKGROUND OF THE INVENTION

Purified forms of glucosyltransferase (GTF) have been found previously to be effective in immunizing animals against dental caries. The purified GTF typically may be employed in a vaccine, which vaccine is administered orally or into or near the oral cavity of a patient susceptible to dental caries, to provide for immunization of the patient against dental caries (see, for example, U.S. Pat. No. 4,150,116, issued Apr. 17, 1979).

GTF has been prepared by a method in which it is derived from the culturing of Streptococcus mutans in the presence of glucose and dialyzable nutrients, to form a mixture of culture cells and a supernatant containing the GTF. The supernatant is subsequently incubated with a sucrose which is synthesized slowly in situ to a water-insoluble polysaccharide. The GTF is recovered from the bound, water-insoluble polysaccharide by the employment of a denaturing solvent, to break the bond between the polysaccharide and the GTF enzyme, and the GTF enzyme is recovered and is subsequently concentrated in purified form by gel filtration (see, for example, U.S. Pat. No. 4,250,262, issued Feb. 10, 1981).

The method of preparing GTF as described, while suitable for the preparation of small laboratory or test amounts of GTF, is not wholly suitable for the production of GTF for pilot or commercial use, wherein the time of preparation, the efficiency of reaction and the recovery of materials are desirable, in order to provide for an effective cost-efficient process. Furthermore, the eluted GTF contains a large amount of soluble glucan which must be removed by gel filtration.

SUMMARY OF THE INVENTION

The invention relates to a method for the preparation of glucosyltransferase (GTF) and more particularly relates to an improved method for the preparation of GTF employing a reusable, polymerized polysaccharide in particulate form.

The present invention is directed toward a method for the large-scale production of GTF from Streptococcus mutans, and which method represents an improvement on the method as described in U.S. Pat. No. 4,250,262, which patent is hereby incorporated by reference in its entirety. The improved method of this invention avoids the time-consuming step of incubating the recovered supernatant from the Streptococcus mutans reaction with sucrose, in order to synthesize, in the clear supernatant, the water-insoluble polysaccharide which becomes bound to the GTF. In addition, the recovered GTF does not contain the large amount of soluble glucan which must be removed by gel filtration when GTF is removed from the water-insoluble polysaccharide synthesized in situ from sucrose. The prior method of incubating the recovered supernatant containing the GTF with sucrose, while desirable and effective, has certain disadvantages in connection with scaling up of the process for pilot-plant or commercial use, and further does not provide for the recovery of any materials for reuse in the process. Thus, the prior method is more time-consuming and does not permit the recovery of materials to reduce the cost of the process and, further, does not readily lend itself to a commercial, continuous process, wherein easily used methods of separation, such as filtration of the solid GTF complex, of the synthesized polysaccharide can be employed.

The improved method of the invention provides for the admixing, directly into the supernatant containing the GTF as derived from the incubation of the Streptococcus mutans with glucose, of a water-insoluble polysaccharide, particularly a cross-linked dextran containing glucose units, such as polyglucan in solid particulate form, directly into the clear supernatant. The solid particulate material, such as in beaded, solid gel form, is admixed with stirring into the supernatant for a period of time sufficient to cause the binding of the GTF to the polyglucan particulate material, such as, for example, from about 38 minutes to 4 hours; to provide for the preparation of the polyglucan-GTF-bound complex, which process may be carried out at varying ranges of temperature; for example, 4° C. to 37° C. Typically, the polyglucan is employed in an amount sufficient for the solid polyglucan particulate to react with the GTF in the supernatant, such as, for example, in a ratio by volume of 1:40 to 1:10 of the polyglucan to the supernatant, and more particularly about 1:20.

The solid-bead polysaccharide employed may be in the form of a solid, particulate, bead-like material commercially sold and used for gel permeation chromotography and known as Sephadex (a trademark of Pharmacia Fine Chemicals, Inc.). The Sephadex material useful in the method comprises a water-insoluble material composed of microscopic beads comprising synthetic organic compounds derived from the polysaccharide dextran. The dextran chains in the material are cross-linked, to provide a three dimensional, gel-like network, and the functional ionic groups are attached to glucose units of the polysaccharide chain by ether linkages. This material, a similar water-insoluble polysaccharide material containing glucose, will be referred to as polyglucan; that is, a polymer of glucose or containing a polymerized glucose. The polyglucan beads range in size from generally less than about 300 microns in diameter; for example and more typically, from about 10 to 120 microns in average diameter. The preferred polyglucan comprises a polymerized, cross-linked dextran. A polymerized cross-link mutan can also be used wherein a dextran-like polymer is synthesized from sucrose by the GTF enzyme of Streptococcus mutans; however, the synthesized material is not preferred since it may be difficult to remove the enzyme from the synthesis mixture.

The polyglucan beads are added to the clear supernatant after removal of the culture cells. An in situ reaction of the water-insoluble polyglucan with the GTF in the supernatant occurs after addition and stirring, to form the polyglucan-GTF complex. Any of the unbound GTF material and the unbound medium components may be removed easily by filtration or centrifugal techniques, to recover the solid-bead, polyglucan-GTF complex, which beads are then washed typically by filtration, which is made possible by the use of the solid-bead form of the complex. The GTF is then recovered by elution with the denaturing solvent, such as guanidine hydrochloride, as described in U.S. Pat. No. 4,250,262. The separated GTF enzyme is then concentrated in the denaturing solvent and purified, such as by gel filtration. Importantly, the separated polyglucan beads, after removal of the GTF by the denaturing solvent, are recovered and reused in the method.

The present method eliminates the need for a long incubation period of the sucrose with the supernatant, to form, after incubation, water-insoluble polysaccharide; thus, saving the time of incubation. The present method also facilitates the preparation of the GTF, since filtration, preferably continuous in commercial production, may be used throughout with the bead polyglucan material as a method of washing and collection of the beads, rather than to collect and to separate the dense in situ particles of the synthesized, water-insoluble polysaccharide by other techniques, such as centrifugation. The present method leads to fewer losses of material, which represents a problem with large scale application of the prior-art laboratory technique. The use of filtration to remove the solid bead material also permits the method to be employed in a continuous manner, and, also importantly, permits the easy recovery; for example, by filtration or centrifugation, and reuse of the polymerized polyglucan, such as Sephadex gel spheres or bead-like material, and reduces the cost of production. The initial cost in the purchasing of the dextran gel spheres is overcome by the ability to use the polyglucan bead material in the method, avoiding the continuous expense of purchasing sucrose for synthesis.

The method of the invention represents a substantial improvement in the preparation of GTF, particularly in purified form, for use in the immunization against dental caries, and provides for significant advantages over the prior-art method of preparation.

The method of the invention will be described in particular with regards to a preferred embodiment; however, it is recognized that various changes, additions and improvements may be made by those persons skilled in the art in the described embodiment, all falling within the spirit and scope of the present invention.

DESCRIPTION OF THE EMBODIMENTS

Glucosyltransferase from a *Streptococcus mutans*, using an externally supplied, insoluble polyglucan to adsorb the GTF from culture supernatants, is prepared as follows:

*Streptococcus mutans* organisms were grown anaerobically (10% $CO_2$, 90% $N_2$) for 24 hours at 37° C. in 2 liters of chemically defined media containing glucose as the carbon source (see Infection and Immunity 23: 445–452 (1979) and J. Dent. Res. 52: 88 (1973) for details on media and conditions). Cells were then removed by centrifugation at 13,700×g for 15 mins. at 4° C. 0.02% sodium azide was then added to inhibit bacterial growth.

Cell-free supernatant is brought to room temperature. To the cell-free supernatant is added 5% by volume of fully swelled Sephadex G-150 in 0.02% sodium azide. Sephadex is a polyglucan gel in bead form and is synthesized by cross-linking dextran with epichlorohydrin. These dextrans are derived from native dextran produced by *Leuconostoc mesenteroides* strain B-512 and are composed of about 95% a-(1-6)-linkages with small numbers of a-(1-4)-linkages at branch points (Lindberg and Svenson, Structural studies on dextran from *Leuconostoc mesenteroides* NRRL B-512, Acta. Chem. Scand. 22: 1907–1912 (1968)). Other Sephadex gels of different sizes (for example, G-10 and G-25), to which GTF will bind, also may be used. The gels are mixed with the cell-free supernatant at 37° C. in a shaking water bath for 2 to 4 hours. The beads (to which GTF is now bound) are removed by filtration on Nalgene (a trademark of Nalge Co., Inc.) 500 ml, 0.2 micron filter units. Beads also can be collected by centrifugation. The beads are washed with 2 to 4 liters of PBS-sodium asize to remove unbound material.

GTF-Sephadex G-150 beads are suspended in an equal volume of 6M guanidine hydrochloride and incubated at 37° C. for 2 hours. These procedures removed approximately 90% of the GTF from the culture supernatant, based on chemical analysis (Somogyi technique) of enzymatic activity. The GTF-containing eluate is separated from the beads by filtration on Nalgene 100 ml, 0.2 micron filter units. 0.45 micron units also can be used, since the bead sizes are well in excess of 40 microns, according to the Pharmacia literature. To increase the yield of GTF, the beads can be reincubated with the culture supernatant and re-eluted with a second volume of 6M guanidine hydrochloride and filtered as above.

The eluate is then concentrated by negative pressure dialysis and gel-filtered on a column of Sepharose CL-4B (a trademark of Pharmacia Fine Chemicals, Inc.), a highly cross-linked 4% agarose. 6M guanidine hydrochloride is used as the eluting buffer. Negligible carbohydrate is detected by the phenol-$H_2SO_4$ assay (Dubois et al). GTF of high specific activity elutes midway in the elution profile. These fractions contain little carbohydrate, some protein and much water-insoluble glucan-synthesizing activity. The ratio of water-insoluble to water-soluble glucan synthetic activity is 5:1 to 10:1 (depending upon the fractions), when *Streptococcus mutans* strain 6715 is used as the source of GTF. These fractions synthesize glucan in the absence of primer, but show increased incorporation of $^{14}C$-glucose from labelled sucrose in the presence of primer dextran T-10 (Pharmacia). The GTF fractions also form a single band of water-insoluble polysaccharide forming activity, when assayed by polyacrylamide gel electrophoresis (5% separating gels), which corresponds to a protein-staining band on duplicate gels.

What is claimed is:

1. A method for preparing glucosyltransferase (GTF) useful for immunization against dental caries, which method comprises:
    (a) culturing *Streptococcus mutans* in a medium containing glucose and dialyzable nutrients, to form a mixture of culture cells and supernatant, the supernatant containing GTF;
    (b) removing the culture cells and recovering the culture supernatant containing the GTF;
    (c) admixing the supernatant containing the GTF with a water-insoluble polyglucan in solid particulate bead form, for a time period sufficient to provide for the binding of the GTF to the polyglucan bead material, to provide a GTF-polysaccharide bead complex;
    (d) recovering the GTF water-insoluble bead complex from the supernatant;
    (e) washing the GTF water-insoluble polysaccharide complex to remove unbound GTF and medium compounds from the polyglucan bead material;
    (f) contacting the GTF water-insoluble polyglucan bead complex with a denaturing solvent, to break the bond between the water-insoluble polyglucan and the GTF, to provide a GTF-denaturing solvent mixture;
    (g) recovering the water-insoluble polyglucan bead material; and (h) concentrating the GTF and purifying the GTF by gel filtration in the denaturing solvent.

2. The method of claim 1 which includes reusing in the method the recovered water-insoluble, solid-bead, polyglucan material.

3. The method of claim 1 wherein the volume amount of the solid polyglucan bead material admixed with the supernatant ranges from about 1:10 to 1:40.

4. The method of claim 1 wherein the solid bead material comprises a material having an average particle size ranging from about 10 to 300 microns.

5. The method of claim 1 wherein the solid polyglucan bead material comprises a cross-linked, gel-like, dextran or mutan material.

6. The method of claim 1 which includes recovering the water-insoluble, polyglucan bead material by filtering the GTF-complex bead material from the supernatant.

7. The method of claim 1 which includes washing the unbound GTF and medium components from the water-insoluble, polyglucan GTF-complex bead material by filtration.

8. The method of claim 1 wherein the supernatant containing the GTF and the water-insoluble polyglucan bead material are admixed for a time period of from about 30 minutes to 4 hours.

9. The method of claim 1 wherein the denaturing solvent comprises a guanidine hydrochloride.

10. A method for preparing glucosyltransferase (GTF) useful for immunization against dental caries, which method comprises:
(a) culturing *Streptococcus mutans* in a medium containing glucose and dialyzable nutrients, to form a mixture of culture cells and supernatant, the supernatant containing GTF;
(b) removing the culture cells and recovering the culture supernatant containing the GTF;
(c) admixing the supernatant containing the GTF with a water-insoluble polyglucan in solid particulate bead form, having an average particle size ranging from about 10 to 300 microns, for a time period sufficient to provide for the binding of the GTF to the polyglucan bead material, to provide a GTF-polysaccharide bead complex;
(d) recovering the GTF water-insoluble bead complex from the supernatant;
(e) washing by filtration the GTF water-insoluble polysaccharide complex to remove unbound GTF and medium compounds from the polyglucan bead material;
(f) contacting the GTF water-insoluble polyglucan bead complex with a denaturing solvent, to break the bond between the water-insoluble polyglucan and the GTF, to provide a GTF-denaturing solvent mixture;
(g) recovering the water-insoluble polyglucan bead material by filtering the GTF-complex bead material from the supernatant;
(h) concentrating the GTF and purifying the GTF by gel filtration in the denaturing solvent; and
(i) reusing in the method the recovered water-insoluble, solid-bead, polyglucan material.

11. The method of claim 10 wherein the solid polyglucan bead material comprises a cross-linked, gel-like, dextran or mutan material.

12. The method of claim 10 wherein the volume amount of the solid polyglucan bead material admixed with the supernatant ranges from about 1:10 to 1:40.

13. The method of claim 10 wherein the polyglucan bead material comprises cross-linked dextran, which dextran is produced by *Leuconostoc mesenteroides* strain B-512.

14. The method of claim 10 wherein the polyglucan bead material comprises a cross-linked dextran material composed of about 95% a-(1-6)-linkages.

* * * * *